US00PP24415P3

(12) United States Plant Patent
Willems

(10) Patent No.: US PP24,415 P3
(45) Date of Patent: Apr. 29, 2014

(54) ***HAWORTHIA* PLANT NAMED 'AMSTERDAM'**

(50) Latin Name: *Haworthia fasciata*
Varietal Denomination: AMSTERDAM

(75) Inventor: Rogier Willems, Tielen (BE)

(73) Assignee: WanDer. Tuinier BV, Krimpen a/d Ijssel (NL)

( * ) Notice: Subject to any disclaimer, the term of this patent is extended or adjusted under 35 U.S.C. 154(b) by 91 days.

(21) Appl. No.: 13/507,696

(22) Filed: Jul. 20, 2012

(65) Prior Publication Data

US 2014/0026272 P1 Jan. 23, 2014

(51) Int. Cl.
*A01H 5/00* (2006.01)

(52) U.S. Cl.
USPC ..... Plt./373

(58) Field of Classification Search
None
See application file for complete search history.

(56) References Cited

U.S. PATENT DOCUMENTS

PP22,241 P3 * 11/2011 Lock ..... Plt./373

OTHER PUBLICATIONS

UPOV PLUTO 2013/04 Citation for 'Amsterdam' Feb. 15, 2012.*

* cited by examiner

*Primary Examiner* — Wendy C Haas

(57) ABSTRACT

A new and distinct *Haworthia* cultivar named 'AMSTERDAM' is disclosed, characterized by a small number of leaves per plant, and unique small white spots on the leaves. The new variety is a *Haworthia*, normally produced as an outdoor garden or container plant.

1 Drawing Sheet

Latin name of the genus and species: *Haworthia fasciata.*
Variety denomination: 'AMSTERDAM'.

BACKGROUND OF THE INVENTION

The new *Haworthia* cultivar is a product of a planned breeding program conducted by the inventor, Rogier Willems, in Tielen, Belgium. The objective of the breeding program was to produce new *Haworthia* varieties for ornamental commercial applications. The cross resulting in this new variety was made before 2008, exact date unknown.

The seed parent is a unpatented, unnamed, proprietary seedling variety of *Haworthia fasciata*. The pollen parent is unknown, as the crossing resulting in 'AMSTERDAM' was an open pollination, with unidentifiable pollen parents. The new variety was discovered in July 2008 by the inventor in a group of seedlings resulting from the crossing, in a research greenhouse in Tielen, Belgium.

Asexual reproduction of the new cultivar 'AMSTERDAM' by tissue culture and vegetative cuttings was first performed at a research greenhouse in Tielen, Belgium in July 2008 and has shown that the unique features of this cultivar are stable and reproduced true to type in successive generations.

SUMMARY OF THE INVENTION

The cultivar 'AMSTERDAM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AMSTERDAM' These characteristics in combination distinguish 'AMSTERDAM' as a new and distinct *Haworthia* cultivar:

1. Small quantity of leaves.
3. Small white dots on leaves

Plants of the new cultivar 'AMSTERDAM' are similar to plants of the seed parent in most horticultural characteristics, however, plants of the new cultivar 'AMSTERDAM' produce white on the inside of the leaf, whereas the seed parent does not. 'AMSTERDAM' also has less leaves than the seed parent.

COMMERCIAL COMPARISON

Plants of the new cultivar 'AMSTERDAM' are similar to plants of the commercial variety of *Haworthia fasciata* known as 'Concolor', unpatented in most horticultural characteristics. However, plants of the new cultivar 'AMSTERDAM' produce leaves with more white spots on leaf overall, as well as larger white spots on leaves, compared to 'Concolor'. 'AMSTERDAM' also has fewer leaves than 'Concolor'.

BRIEF DESCRIPTION OF THE PHOTOGRAPHS

The accompanying photograph in FIG. 1 illustrates in full color a typical plant of 'AMSTERDAM' grown in a greenhouse, in a 8.5 cm pot. Age of the plant photographed is approximately 18 months from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2005 except where general terms of ordinary dictionary significance are used. The following observations and measurements describe 'AMSTERDAM' plants in a greenhouse in Tielen, Belgium. The growing temperature ranged from 18° C. to 28° C. during the day and from 13° C. to 18° C. during the night. General light conditions are bright, normal sunlight. Measurements and numerical values represent averages of typical plant types. Plants are approximately 18 months old from a rooted cutting.

Botanical classification: *Haworthia fasciata* 'AMSTERDAM'.

PROPAGATION

Time to initiate roots: About 70 days at approximately 20-28° C.

Root description: Moderately thick, moderately branched, slightly fibrous, slightly fleshy, coloured near RHS Greyed-Yellow 161C.

Propagation method: Vegetative divisions or tissue culture.

PLANT

Growth habit: Upright, from basal rosettes; no stems or lateral branches present.

Height: Approximately 5.5 cm to top of highest leaf.

Plant spread: Approximately 8.5 cm.

Growth rate: Slow.

FOLIAGE

Leaf:

*Arrangement*.—Basal rosette.

*Average length*.—Approximately 3.9 cm.

*Average width*.—Approximately 1.2 cm (measured at ⅓ from the base).

*Shape of blade*.—Narrow lanceolate, very slightly arching.

*Apex*.—Narrow acute.

*Base*.—Broad cuneate.

*Margin*.—Entire.

*Texture of top surface*.—Pustulate.

*Texture of bottom surface*.—Pustulate, as dots and connected to axillary bands.

*Quantity of leaves per plant*.—Approximately 40.

*Color*.—Young foliage upper side: Near RHS Green N137C and N137D, base lighter; 145A, leaf covered with small dots (pustulate), colored near RHS White N155D. Young foliage under side: Near RHS N137D, base lighter; Yellow-Green 145A. Leaf covered with very small dots (pustulate) connected to axillary stripes, both colored near RHS White N155D. Mature foliage upper side: A color in between RHS Green 139A and Yellow-Green 147A, base lighter; Yellow-Green 144B, leaf covered with very small dots (pustulate), colored near RHS White N155D. Average diameter of dots: 0.75 mm. Mature foliage under side: A color in between RHS 137D and 147A, base lighter; Yellow-Green 152D leaf covered with very small dots (pustulate) connected to axillary stripes, colored near RHS White N155D. Average width of stripes: 1 mm, stripes are placed approximately 2.5 mm apart from each other.

*Venation*.—Type: Linear. Venation color upper side: A color in between RHS Green 139A and Yellow-Green 147A, base lighter; Yellow-Green 144B. Venation color under side: A color in between RHS Green 137D and Yellow-Green 147A, base lighter; Yellow-Green 152D.

FLOWER

No flowers observed to date:

OTHER CHARACTERISTICS

Seeds and fruits: No seed or fruit observed to date.

Disease/pest resistance: Neither resistance nor susceptibility to diseases and pests has been observed.

Temperature tolerance: Tolerates temperatures from approximately 5° C. to 45° C.

What is claimed is:

1. A new and distinct cultivar of *Haworthia* plant named 'AMSTERDAM' as herein illustrated and described.

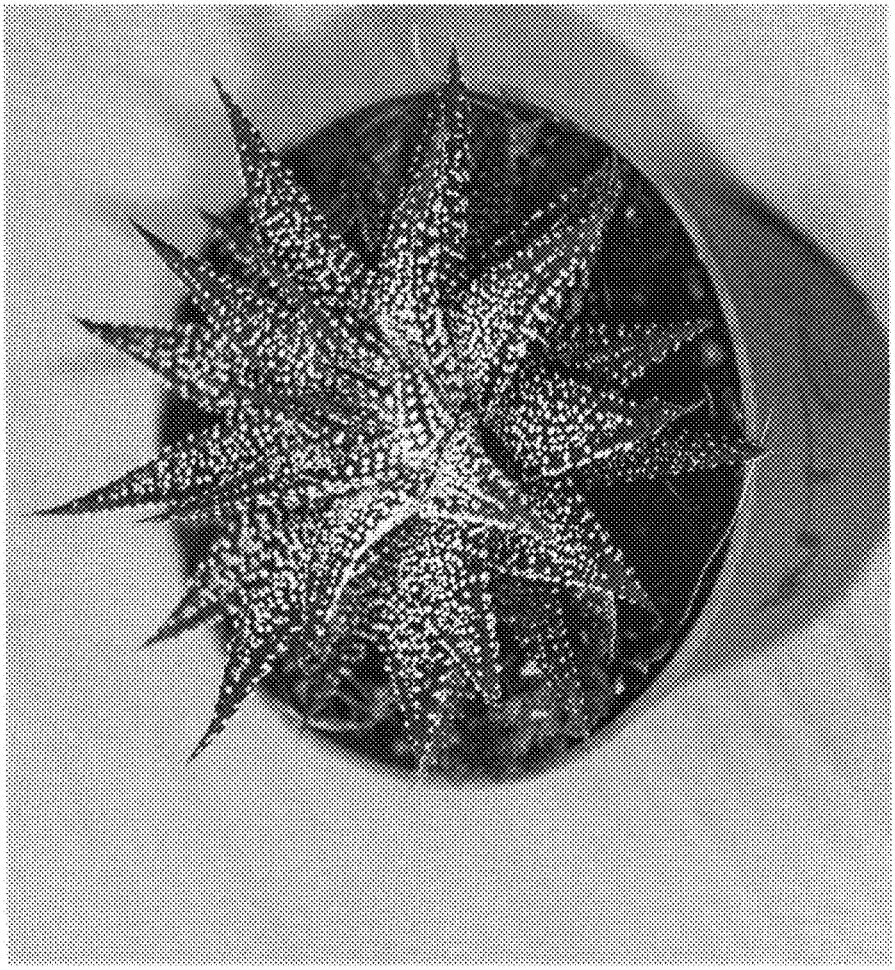

* * * * *